United States Patent [19]

Treasurywala et al.

[11] 4,337,265

[45] Jun. 29, 1982

[54] CYCLOHEPTA[B]PYRROLE DERIVATIVES

[75] Inventors: Adi Treasurywala, Pointe Claire; Bozidar Palameta, Dollard des Ormeaux; Tibor Bogri, St. Laurent; Jehan Bagli, Kirkland, all of Canada

[73] Assignee: Ayerst, McKenna & Harrison Inc., Montreal, Canada

[21] Appl. No.: 295,178

[22] Filed: Aug. 21, 1981

[51] Int. Cl.³ .................. C07D 209/52; A61K 31/40; A61K 31/55
[52] U.S. Cl. ...................................... 424/274; 548/512
[58] Field of Search ..................... 260/326.27; 424/274

[56] References Cited

U.S. PATENT DOCUMENTS

| | | | |
|---|---|---|---|
| 3,106,559 | 10/1963 | Sunagawa et al. | 260/326.27 |
| 3,230,234 | 1/1966 | Sunagawa et al. | 260/326.27 |
| 3,311,641 | 3/1967 | Sunagawa et al. | 260/326.27 |
| 3,821,383 | 6/1974 | Sestanj et al. | 424/258 |

FOREIGN PATENT DOCUMENTS 38-1383 of 1963 Japan .
39-12930 7/1964 Japan ............... 260/326.27
39-17288 8/1964 Japan ............... 260/326.27
39-12929 8/1964 Japan ............... 260/326.27

OTHER PUBLICATIONS

Nozoe et al.; Chem. Abs., vol. 49: 13219f, (1954).
Kikuchi et al.; Chem. Abs., vol. 90: 6139g, (1979).
Dvornik et al.; Science, vol. 182, p. 1146 (1973).
Peterson et al.; Metabolism, vol. 28 (Suppl. 1), p. 456 (1979).
Sunagawa et al.; Chem. Abs., vol. 58: 6773c (1963).
Sunagawa et al.; Chem. Abs., vol. 60: 2971f (1963).

*Primary Examiner*—Mary C. Lee
*Attorney, Agent, or Firm*—Arthur E. Wilfond

[57] ABSTRACT

Disclosed herein are 1,2-dihydro-2-oxo(or 2-thioxo)cyclohepta[b]-pyrrole-1-acetic acid derivatives having optional substitution at positions 3, on the cycloheptatriene ring and on the acetic acid side chain. The compounds are aldose reductase inhibitors and thus are useful for treating diabetic complications.

22 Claims, No Drawings

CYCLOHEPTA[B]PYRROLE DERIVATIVES

This application relates to cyclohepta[b]pyrrole derivatives, therapeutically acceptable salts thereof, a process for their preparation, and to methods of use and to pharmaceutical compositions thereof. The derivatives have pharmacologic properties which render beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their wellbeing and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galacitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. (S)-6-Fluoro-2,3-dihydrospiro(4H-1-benzopyran-4,4'-imidazolidine)-2',5'-dione (sorbinil) is still another compound that has received attention because of its aldose reductase inhibiting properties, see M. J. Peterson et al., Metabolism, 28 (Suppl. 1), 456 (1979). Accordingly, these compounds represent an important new approach for the treatment of diabetes mellitus.

The present application discloses novel cyclohepta[b]pyrrole derivatives, which are effective inhibitors of aldose reductase. These new derivatives are structurally quite different from the above noted aldose reductase inhibitors. A closely related prior art compound, on a structural basis, appears to be 3-methyl-8-(1H)-oxocyclohepta[b]pyrrole-1-acetic acid ethyl ester, see Chem. Abstr., 58, 6773 c (1963) for G. Sunagawa and Y. Sato, Yakugaku Zasshi, 82, 408 (1962), and Chem. Abstr., 60, 2971 f (1965) for G. Sunagawa and Y. Sato, Japanese Patent No. 1383 (1963). The prior art compound is distinguished from the present compounds by the nature of the substituents on the cyclohepta[b]pyrrole ring system.

SUMMARY OF THE INVENTION

The cyclohepta[b]pyrrole derivatives of this invention are represented by formula I

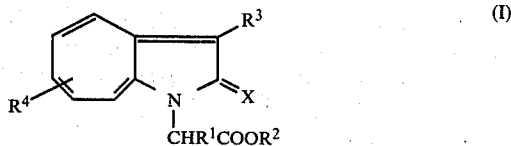

in which $R^1$ is hydrogen, carboxymethyl or lower alkoxycarbonylmethyl; $R^2$ is hydrogen, lower alkyl or (2,2-dimethyl-1-oxopropoxy)methyl; $R^3$ is hydrogen, lower alkyl, 1-oxo(lower)alkyl, carboxy, lower alkoxycarbonyl, (2,2-dimethyl-1-oxopropoxy)methoxycarbonyl, cyano, aminocarbonyl or $CON(R^5)CH_2COOR^6$ wherein $R^5$ is lower alkyl and $R^6$ is hydrogen or lower alkyl; $R^4$ is hydrogen, lower alkyl, lower alkoxy or halo; and X is oxo or thioxo; with the provisos that when $R^1$ is carboxymethyl then $R^2$ is hydrogen, that when $R^1$ is lower alkoxycarbonylmethyl then $R^2$ is lower alkyl, that when $R^2$ is (2,2-dimethyl-1-oxopropoxy)methyl then $R^1$ is hydrogen and $R^3$ is (2,2-dimethyl-1-oxopropoxy)methoxycarbonyl, that when $R^6$ is hydrogen then $R^1$ is hydrogen or carboxymethyl and $R^2$ is hydrogen, that when $R^6$ is lower alkyl then $R^1$ is hydrogen or lower alkoxycarbonylmethyl and $R^2$ is lower alkyl, that when $R^3$ is hydrogen then $R^1$ is hydrogen or carboxymethyl and $R^2$ is hydrogen, and that when X is thio then $R^1$ is hydrogen, $R^2$ is hydrogen, lower alkyl or (2,2-dimethyl-1-oxopropoxy)methyl, and $R^3$ is carboxy, lower alkoxycarbonyl or (2,2-dimethyl-1-oxopropoxy)methoxycarbonyl; or a therapeutically acceptable salt, with an organic or inorganic base, of the compound of formula I having one or more carboxyls.

A preferred group of compounds is represented by formula I in which $R^1$ is hydrogen, carboxymethyl, methoxycarbonylmethyl or ethoxycarbonylmethyl; $R^2$ is hydrogen, methyl, ethyl or (2,2-dimethyl-1-oxopropoxy)methyl; $R^3$ is hydrogen, methyl, ethyl, acetyl, carboxy, methoxycarbonyl, ethoxycarbonyl, (2,2-dimethyl-1-oxopropoxy)methoxycarbonyl, cyano, aminocarbonyl or $CON(CH_3)CH_2COOR^6$ wherein $R^6$ is hydrogen, methyl or ethyl; $R^4$ is hydrogen or chloro and X is oxo or thioxo; with the provisos that when $R^1$ is carboxymethyl then $R^2$ is hydrogen, that when $R^1$ is methoxycarbonylmethyl or ethoxycarbonylmethyl then $R^2$ is methyl or ethyl, that when $R^2$ is (2,2-dimethyl-1-oxopropoxy)methyl then $R^1$ is hydrogen and $R^3$ is (2,2-dimethyl-1-oxopropoxy)methoxycarbonyl, that when $R^6$ is hydrogen then $R^1$ is hydrogen or carboxymethyl and $R^2$ is hydrogen, that when $R^6$ is methyl or ethyl then $R^1$ is hydrogen, methoxycarbonylmethyl or ethoxycarbonylmethyl and $R^2$ is methyl or ethyl, that when $R^3$ is hydrogen then $R^1$ is hydrogen or carboxymethyl and $R^2$ is hydrogen and that when X is thioxo then $R^1$ is hydrogen and $R^3$ is carboxy, methoxycarbonyl, ethoxycarbonyl or (2,2-dimethyl-1-oxopropoxy)methoxycarbonyl.

A more preferred group of compounds is represented by formula I in which $R^1$ and $R^2$ each is hydrogen, $R^3$ is carboxy, acetyl or cyano, $R^4$ is hydrogen or 6-chloro and X is oxo or thioxo; with the proviso that when X is thioxo then $R^3$ is carboxy.

The compounds of formula I can be prepared by a process described hereinafter.

A method is provided for preventing or relieving diabetes mellitus associated complications in a diabetic mammal by administering to said mammal a prophylactic or alleviating amount of the compound of formula I or therapeutically acceptable salt thereof with anorganic or inorganic base. These complications include neuropathy, nephropathy, retinopathy and cataracts.

The compounds of formula I, or a therapeutically acceptable salt thereof with an organic or inorganic base, when admixed with a pharmaceutically acceptable carrier, form a pharmaceutical composition which can be used according to the preceding method.

DETAILED DESCRIPTION OF THE INVENTION

The term "lower alkyl" as used herein means a straight chain alkyl radical containing from one to six carbon atoms, preferably one to two carbon atoms, or a branched chain alkyl radical containing three to four carbon atoms and includes methyl, ethyl, propyl, 1-methylethyl, propyl, 2-methylpropyl and 1,1-dimethylethyl.

The term "lower alkoxy" as used herein means straight chain alkoxy radicals containing from one to six carbon atoms, preferably one to three carbon atoms, and branched chain alkoxy radicals containing three or four carbon atoms and includes methoxy, ethoxy, 1-methylethoxy, butoxy, hexanoxy and the like.

The term "1-oxo(lower)alkyl" as used herein means straight chain 1-oxoalkyl radicals containing from two to six carbon atoms, preferably two to three carbon atoms, and branched chain 1-oxoalkoxy radicals containing four to six carbon atoms and includes acetyl, 1-oxopropyl, 1-oxobutyl, 2,2-dimethyl-1-oxopropyl, 1-oxohexyl and the like.

The term "halo" or "halide" as used herein means a halo radical or halide selected from the group consisting of bromine, chlorine, fluorine and iodine.

The term "lower alkanol" as used herein means both straight and branched chain alkanols containing from one to four carbon atoms and includes methanol, ethanol, isopropanol, butanol and the like.

The term "lower alkanoic acid" as used herein means straight chain alkanoic acids containing one to six carbon atoms, preferably one to two carbon atoms, and branched chain alkanoic acids containing four to six carbon atoms and includes acetic, propionic, butyric, 2,2-dimethylpropionic, hexanoic acid and the like.

The term "inorganic proton acceptor" as used herein means the inorganic bases, preferably the alkali metal hydrides, hydroxides and carbonates, or their corresponding lower alkoxides, for example, sodium hydride, potassium hydroxides, sodium carbonate, potassium carbonate, sodium ethoxide and the like.

The term "organic proton acceptor" as used herein means the organic bases or amines, for instance, triethylamine, pyridine, N-ethylmorpholine, 1,5-diazabicyclo[4.3.0]non-5-ene and the like.

The term "proton acceptor" as used herein means a proton acceptor selected from an organic proton acceptor and inorganic proton acceptor, as defined hereinabove.

The compounds of formula I, having one or more free carboxy groups, form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the present therapeutic agents will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 50 mg to about 250 mg per kilo of body weight per day, although aforementioned variations will occur. However, a dosage level that is in the range of from about 100 mg to about 150 mg per kilo of body weight per day is most satisfactory.

Unit dosage forms such as capsules, tablets, pills and the like may contain from about 25 mg to about 500 mg of the active ingredients of this invention, dependent on the type of unit dosage, preferably with a significant quantity of a pharmaceutically carrier. Thus, for oral administration, capsules can contain from between about 25 mg to about 500 mg of the active ingredients of this invention with or without a pharmaceutical diluent. Tablets, either effervescent or noneffervescent, can contain between about 25 to 500 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, and may advantageously contain glycerol and ethyl alcohol as solvents or preservatives.

The compounds of formula I, or their therapeutically acceptable salts, also can be used in combination with insulin or oral hypoglycemic agents to produce beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds of formula I, or their therapeutically acceptable salts, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., U.S., 1980. When used in combination, the compounds of formula I, or their therapeutically acceptable salts, are administered as described previously. The compounds of formula I, or their therapeutically acceptable salts, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the foregoing listed compounds of formula I were evaluated in the above in vitro test.

| Compounds of Formula I | | | | | Example In Which Compound Is Prepared | % Inhibition At Different Molar Concentrations (in vitro) | | |
|---|---|---|---|---|---|---|---|---|
| $R^1$ | $R^2$ | $R^3$ | $R^4$ | X | | $10^{-5}$ | $10^{-6}$ | $10^{-7}$ |
| H | H | COOH | H | O | 2 | 88 | 82 | 44 |
| H | H | H | H | O | 3 | 80 | 45 | 9 |
| H | H | COOC$_2$H$_5$ | H | O | 4 | 73 | 26 | |
| H | H | COOH | H | S | 5 | 93 | 85 | 47 |
| H | CH$_2$OCOC—(CH$_3$)$_3$ | COOCH$_2$OCO—(CH$_3$)$_3$ | H | O | 6 | 75 | 44 | 9 |
| H | H | COCH$_3$ | H | O | 7 | 76 | 26 | 3 |
| H | H | C$_2$H$_5$ | H | O | 8 | 60 | 19 | |
| H | H | COOH | 6-Cl | O | 9 | 85 | 78 | 36 |
| H | H | COOC$_2$H$_5$ | 6-Cl | O | 10 | 76 | 34 | 9 |
| H | H | COCH$_3$ | 6-Cl | O | 11 | 85 | 52 | 11 |
| H | H | CN | H | O | 12 | 88 | 82 | 48 |

-continued

| Compounds of Formula I | | | | | Example In Which Compound Is Prepared | % Inhibition At Different Molar Concentrations (in vitro) | | |
|---|---|---|---|---|---|---|---|---|
| $R^1$ | $R^2$ | $R^3$ | $R^4$ | X | | $10^{-5}$ | $10^{-6}$ | $10^{-7}$ |
| H | H | $CONH_2$ | H | O | 13 | 73 | 28 | 7 |

Preparation of the Compounds

The compounds of formula I can be prepared by one of the following processes:

(a) condensing a compound of formula II

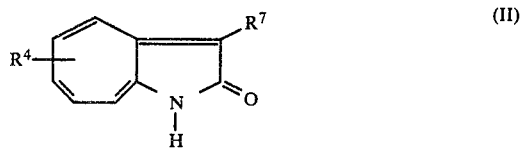

in which $R^4$ is hydrogen, lower alkyl, lower alkoxy or halo and $R^7$ is lower alkyl, 1-oxo(lower)alkyl, lower alkoxycarbonyl, cyano or $CON(R^5)CH_2COOR^6$ wherein $R^5$ and $R^6$ each is lower alkyl with a compound of formula III $$Y-CHR^1COO-Alk \qquad (III)$$

wherein Y is bromo, chloro or iodo, $R^1$ is hydrogen or lower alkoxycarbonylmethyl and Alk is lower alkyl to obtain the corresponding compound of formula I in which $R^1$ is hydrogen or lower alkoxycarbonylmethyl, $R^2$ is lower alkyl, $R^3$ is lower alkyl, 1-oxo(lower)alkyl, lower alkoxycarbonyl, cyano or $CON(R^5)CH_2COOR^6$ wherein $R^5$ and $R^6$ each is lower alkyl, $R^4$ is defined herein and X is oxo;

(b) selectively hydrolyzing the compound of formula I in which $R^1$ is hydrogen or lower alkoxycarbonylmethyl, $R^2$ is lower alkyl, $R^3$ is lower alkoxycarbonyl, $R^4$ is as defined herein and X is oxo with about one equivalent of a strong base to obtain the corresponding compound of formula I in which $R^1$ is hydrogen or carboxymethyl, $R^2$ is hydrogen, $R^3$ is lower alkoxycarbonyl, $R^4$ is as defined herein, and X is oxo;

(c) selectively hydrolyzing the compound of formula I in which $R^1$ is hydrogen or lower alkoxycarbonylmethyl, $R^2$ is lower alkyl, $R^3$ is cyano, $R^4$ is as defined herein and X is oxo with a strong mineral acid in the presence of sufficient water to obtain the corresponding compound of formula I in which $R^1$, $R^2$, $R^4$ and X are as defined in the last instance and $R^3$ is aminocarbonyl;

(d) hydrolyzing the compound of formula I in which $R^1$ is hydrogen or lower alkoxycarbonylmethyl, $R^2$ is lower alkyl, $R^3$ is lower alkyl, 1-oxo(lower)alkyl, lower alkoxycarbonyl, cyano, aminocarbonyl or $CON(R^5)CH_2COOR^6$ wherein $R^5$ and $R^6$ each is lower alkyl, $R^4$ is as defined herein and X is oxo to obtain the corresponding compound of formula I in which $R^1$ is hydrogen or carboxymethyl, $R^2$ is hydrogen, $R^3$ is lower alkyl, 1-oxo(lower)alkyl, carboxy, cyano, aminocarbonyl or $CON(R^5)CH_2COOR^6$ wherein $R^5$ is lower alkyl and $R^6$ is hydrogen, $R^4$ is as defined herein, and X is oxo;

(e) decarboxylating the compound of formula I in which $R^1$, $R^2$, $R^4$ and X are as defined in the last instance and $R^3$ is carboxy to obtain the corresponding compound of formula I in which $R^3$ is hydrogen;

(f) esterifying the compound of formula I in which $R^1$ is hydrogen or carboxymethyl, $R^2$ is hydrogen, $R^3$ is hydrogen, lower alkyl, 1-oxo(lower)alkyl, carboxy, cyano, aminocarbonyl or $CON(R^5)CH_2COOR^6$ wherein $R^5$ is lower alkyl and $R^6$ is hydrogen, $R^4$ is as defined herein and X is oxo to obtain the corresponding compound of formula I in which $R^1$ is hydrogen or lower alkoxycarbonylmethyl, $R^2$ is lower alkyl, $R^3$ is hydrogen, lower alkyl, 1-oxo(lower)alkyl, lower alkoxycarbonyl, cyano, aminocarbonyl or $CON(R^5)CH_2COOR^6$ wherein $R^5$ is lower alkyl and $R^6$ is lower alkyl, $R^4$ is as defined herein and X is oxo;

(g) esterifying the compound of formula I in which $R^1$ and $R^2$ each is hydrogen, $R^3$ is carboxy, $R^4$ is as defined herein and X is oxo with 2,2-dimethylpropionic acid halomethyl ester in the presence of a proton acceptor to obtain the corresponding compound of formula I in which $R^1$ is hydrogen, $R^2$ is (2,2-dimethyl-1-oxopropoxy)methyl, $R^3$ is (2,2-dimethyl-1-oxopropoxy)methoxycarbonyl, $R^4$ is as defined herein and X is oxo;

(h) reacting the compound of formula I in which $R^1$ is hydrogen, $R^2$ is lower alkyl or (2,2-dimethyl-1-oxopropoxy)methyl, $R^3$ is lower alkoxycarbonyl, or (2,2-dimethyl-1-oxopropoxy)methoxycarbonyl, $R^4$ is as defined herein and X is oxo with phosphorus pentasulfide to obtain the corresponding compound of formula I in which $R^1$, $R^2$, $R^3$ and $R^4$ are as defined in the last instance and X is thioxo; and, if required, selectively hydrolyzing the last-named compound to obtain the corresponding compound of formula I in which $R^1$ and $R^2$ each is hydrogen, $R^3$ is lower alkoxycarbonyl or (2,2-dimethyl-1-oxopropoxy)methoxycarbonyl, $R^4$ is as defined herein and X is thio, or hydrolyzing said last-named compound to obtain the corresponding compound of formula I in which $R^1$ and $R^2$ each is hydrogen, $R^3$ is carboxy, $R^4$ is as defined herein and X is thio; and if desired, (i) forming a therapeutically acceptable salt with an organic or inorganic base of the compounds of formula I having one or more carboxyl groups.

More specifically, with reference to above paragraph (a), the compounds of formula I in which $R^1$ is hydrogen or lower alkoxycarbonylmethyl, $R^2$ is lower alkyl, $R^3$ is lower alkyl, 1-oxo(lower)alkyl, lower alkoxycarbonyl, cyano or $CON(R^5)CH_2COOR^6$ wherein $R^5$ and $R^6$ each is lower alkyl, $R^4$ is as defined herein and X is oxo can be prepared by condensing the compound of formula II, as defined herein, with the compound of formula III, as defined herein, in the presence of a proton acceptor.

Practical and convenient conditions for effecting the latter condensation include the use of one to two molar equivalents of the proton acceptor. Inorganic proton acceptors, for example, sodium hydride, sodium hydroxide or potassium carbonate, have been found to be suitable proton acceptors. Any solvent, which does not interfere with the reaction, can serve as the reaction medium. Suitable solvents include dimethylformamide, dimethyl sulfoxide, toluene, acetone and tetrahydrofuran. Preferred conditions for effecting the condensation include the use of sodium hydride or potassium carbonate as the proton acceptor and dimethylformamide as the solvent. Although the optimum temperature and reaction time will vary depending on the reactants employed, the reaction is performed generally at 20° to 120° C., or the boiling point of the reaction mixture, for a period of 30 minutes to 48 hours.

The compounds of formula II, required for the above condensation, are either known or can be prepared by known methods. For example, 3-acetyl-1,2-dihydro-2-oxocyclohepta[b]pyrrole is reported by T. Nozoe et al., Bull. Chem. Soc. Japan, 38, 306 (1965); and 1,2-dihydro-2-oxocyclohepta[b]pyrrole-3-carboxylic acid ethyl ester and its corresponding 6-chloro derivative are reported by T. Nozoe et al., Japanese Pat. No. 2217(1957), April 11, 1957; see Chem. Abstr., 52, 6411e (1958). The preparation of the compounds of formula II are exemplified in examples 1, 9, 11 and 12, see hereinafter. In a preferred embodiment 1,2-dihydro-2-oxocyclohepta[b]pyrrole-1-acetic acid ethyl ester, a starting material of formula II, is prepared directly in the form of its sodium salt and the salt is condensed with the above noted compound of formula III.

With reference to paragraph (b), compounds of formula I in which $R^1$ is hydrogen or carboxymethyl, $R^2$ is hydrogen, $R^3$ is lower alkoxycarbonyl, $R^4$ is as defined herein and X is oxo are obtained by selective hydrolysis of the corresponding compound of formula I in which $R^1$ is hydrogen or lower alkoxycarbonylmethyl, $R^2$ is lower alkyl, $R^3$ is lower alkoxycarbonyl, $R^4$ is as defined herein and X is oxo.

The selective hydrolysis is effected by employing one less molar equivalent of a strong base than the number of ester groups present in the last-named compound of formula I. For example, if the compound of formula I to be hydrolyzed has two or three ester groups then one or two molar equivalents of a strong base are employed, respectively. Suitable strong bases for this hydrolysis are, for example, sodium or potassium hydroxide or sodium or potassium carbonate. The hydrolysis is performed in the presence of sufficient water to effect the hydrolysis, and is performed conveniently by using a suitable solvent, for example, methanol or ethanol. The reaction mixture is maintained at a temperature of about 20° to 30° C. until hydrolysis is complete. Usually from 10 minutes to six hours is sufficient. The reaction mixture is then rendered acidic with an acid, for example, acetic acid, hydrochloric acid or sulfuric acid, to release the free acid.

With reference to paragraph (c), compounds of formula I in which $R^1$ is hydrogen or lower alkoxycarbonylmethyl, $R^2$ is lower alkyl, $R^3$ is aminocarbonyl, $R^4$ is as defined herein and X is oxo are obtained by selectively hydrolyzing the compound of formula I in which $R^1$, $R^2$, $R^4$ and X are as defined in the last instance and $R^3$ is cyano. This hydrolysis is done in the presence of a strong mineral acid, for example sulfuric acid or polyphosphoric acid, in the presence of sufficient water to effect hydrolysis. In a preferred embodiment of this hydrolysis, an excess of water in the hydrolysis mixture is avoided and the temperatures and reaction times are minimized to prevent hydrolysis of ester groups present in the compound of formula I. Convenient and practical reaction times and temperatures for this reaction range from one to three hours at 20° to 30° C. Thereafter, the reaction mixture is worked up immediately.

With reference to paragraph (d), compounds of formula I in which $R^1$ is hydrogen or carboxymethyl, $R^2$ is hydrogen, $R^3$ is lower alkyl, 1-oxo(lower)alkyl, carboxy, cyano, aminocarbonyl or $CON(R^5)CH_2COOR^6$ wherein $R^5$ is lower alkyl and $R^6$ is hydrogen, $R^4$ is as defined herein and X is oxo are obtained by hydrolysis of the corresponding compound of formula I in which $R^1$ is hydrogen or lower alkoxycarbonylmethyl, $R^2$ is lower alkyl, $R^3$ is lower alkyl, 1-oxo(lower)alkyl, lower alkoxycarbonyl, cyano, aminocarbonyl or $CON(R^5)CH_2COOR^6$ wherein $R^5$ and $R^6$ each is lower alkyl, $R^4$ is as defined herein and X is oxo in the presence of sufficient water and hydrolyzing agent to effect complete hydrolysis of all the ester groups present in the compound of formula I.

This latter hydrolysis can be performed most conveniently by employing a base as the hydrolyzing agent. However, it should be understood that the manner of this hydrolysis is not to be limited to basic hydrolysis since hydrolysis under acidic conditions and other variations, for example, treatment with lithium iodide in collidine (see L. F. Fieser and M. Fieser, "Reagent for Organic Synthesis", John Wiley & Sons, Inc., New York, 1969, pp. 615–617), also are applicable. Hydrolysis under acidic conditions is preferred for tert butyl esters. Basic hydrolysis is preferred when the compound of formula I has a cyano group which is to be retained.

For basic hydrolysis, a preferred embodiment involves subjecting the compound of formula I to the action of a strong base, for example, sodium hydroxide or potassium hydroxide. The hydrolysis is performed using a suitable solvent, for example, methanol, ethanol or 2-methoxyethanol. The reaction mixture is maintained at a temperature ranging from 25°–100° C. or at the reflux temperature of the solvent employed until hydrolysis is complete. Usually from 10 min to six hours is sufficient. The reaction mixture is then rendered acidic, for example, with acetic acid, hydrochloric acid or sulfuric acid, to release the free acid.

For acid hydrolysis, a preferred embodiment involves subjecting the compound of formula I to the action of a strong organic or inorganic acid, for example, hydrochloric acid, sulfuric acid, trifluoroacetic acid or p-toluenesulfonic acid, in the presence of sufficient water to effect hydrolysis. Suitable solvents include water, the lower alkanols and acetic acid. The reaction mixture is maintained at a temperature ranging from 20°–100° C. or at the reflux temperature of the solvent employed until hydrolysis is complete. Usually a reaction time of 30 minutes to two hours is sufficient.

With reference to paragraph (e), compounds of formula I in which $R^1$ is hydrogen or carboxymethyl, $R^2$ and $R^3$ each is hydrogen, $R^4$ is as defined herein and X is oxo are obtained by decarboxylating the corresponding compound of formula I in which $R^3$ is carboxy. In a preferred embodiment, the decarboxylation is accomplished by subjecting the compound of formula I to the action of a strong mineral acid, for example, hydrochloric acid, polyphosporic acid or sulfuric acid, for a period ranging from six to 24 hours at 25° to 60° C. An inert solvent may be employed for the decarboxylation. Examples of suitable solvents are water and/or the lower alkanols.

With reference to paragraph (f) and (g), esterification is effected by conventional methods. For example, the compound of formula I in which $R^2$ is lower alkyl with optional ester groups at $R^1$ and $R^3$ are obtained by reacting the corresponding acidic compound with an alkanol containing one to six carbon atoms in the presence of an acid catalyst (e.g. sulfuric acid, hydrochloric acid or p-toluenesulfonic acid), or by converting the corresponding acid to its acid chloride which in turn is reacted with an alkanol containing one to six carbon atoms in the presence of a proton acceptor. A preferred embodiment for preparing the compound of formula I in which $R^1$ is hydrogen, $R^2$ is (2,2-dimethyl-1-oxopropoxy)methyl and $R^3$ is (2,2-dimethyl-1-oxopropoxy)methoxycarbonyl, $R^4$ is as defined herein and X is oxo involves reacting the corresponding acid compound with about two to three molar equivalents of 2,2-dimethylpropionic acid chloromethyl ester in the presence of an organic proton acceptor. Suitable organic proton acceptors are, for example, potassium carbonate, pyridine, or N-ethylmorpholine. Convenient times and temperatures for effecting the esterification range from six to 24 hours at 20° to 60° C.

With reference to paragraph (h), the compounds of formula I in which X is thio are obtained by reacting the compound of formula I in which $R^1$ is hydrogen, $R^2$ is lower alkyl or (2,2-dimethyl-1-oxopropoxy)methyl, $R^3$ is lower alkoxycarbonyl or (2,2-dimethyl-1-oxopropoxy)methoxycarbonyl, $R^4$ is as defined herein and X is oxo under anhydrous conditions with about two to five moles of phosphorus pentasulfide in an inert solvent, e.g. xylene or toluene, to obtain the corresponding compound of formula I in which X is thioxo. The reaction is performed conveniently at temperatures ranging from 80° to about 150° C. and times ranging from 20 minutes to four hours. This reaction also can be performed in the presence of an organic base, for instance N-ethylmorpholine or pyridine. Thereafter, if desired, the hydrolysis, or selective hydrolysis is effected in the manner described above for such hydrolysis.

With reference to paragraph (i), the formation of the therapeutically acceptable salts of the compounds of formula I have been described hereinbefore with reference to sections (b) and (d). However, when an inorganic base salt of a compound of formula I is desired, an optional method involves the direct procurement of the compound by basic hydrolysis of the corresponding ester using a strong base having a physiologically compatible cation, for example, Na+, K+ or Ca++. In this instance, a sufficient amount of the base is employed to provide the desired salt. The salt is isolated by evaporating the solvent from the reaction mixture.

In a related aspect of this invention, it has been found that 3-carboxy-1-(carboxymethyl)-cyclohepta[b]pyrrolium halides of the following formula

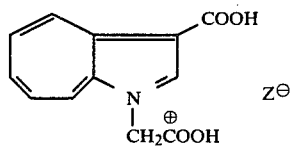

in which Z is halo also exhibits aldose reductase inhibiting properties. For example, in the above noted test, 3-carboxy-1-(carboxymethyl)-cyclohepta[b]pyrrolium chloride exhibited an 80%, 37% and 13% inhibition of aldose reductase at molar concentrations of $10^{-5}$, $10^{-6}$ and $10^{-7}$, respectively. The cyclohepta[b]pyrrolium compound is obtained by heating 2-amino-2,4,6-cycloheptatrien-1-one and diethyl ethoxymethylenemalonate together at 140° C. for two hours to obtain 2-[(7-oxo-1,3,5-cycloheptatrien-1-yl)aminomethylene]-propanedioic acid diethyl ester, dissolving the latter ester in diphenyl ether and heating the solution at 140° C. for ten minutes to obtain a mixture of 4,9-dihydro-4,9-dioxo-1H-cyclohepta[b]pyridine-3-carboxylic acid ethyl ester and cyclohepta[b]pyrrole-3-carboxylic acid ethyl ester which is separated by chromatography, reacting the latter compound with a haloacetic acid lower alkyl ester to obtain the corresponding 3-(lower alkoxycarbonyl)-1-(lower alkoxycarbonylmethyl)-cyclohepta[b]pyrrolium halide and hydrolyzing the last-named compound under acidic conditions to obtain the corresponding 3-carboxy-1-(carboxymethyl)-cyclohepta[b]pyrrolium halide.

The following examples illustrate further this invention.

EXAMPLE 1

1,2-Dihydro-2-oxocyclohepta[b]pyrrole-3-carboxylic Acid Ethyl Ester (II, $R^4$=H and $R^7$=COOC$_2$H$_5$)

Diethyl malonate (150 ml) was added to a 1 liter, round bottomed flask equipped with a magnetic stirring bar. Stirring was commenced and sodium hydride (20 g, 50% dispersion in mineral oil) was added gradually without cooling so as to maintain the internal temperature at 70° to 90° C. (Attention; evolution of hydrogen). When all of the sodium hydride had been added, a thick white spongy cake resulted. To this was added 2-aminotropone (50 g) in solid form and in one portion. Finally, a further small amount (70 ml) of diethyl malonate was added. The resulting dark heterogeneous mass was stirred and immersed in an oil bath which had been preheated to 125° C. The reaction mixture quickly became homogeneous but became a solid yellow cake as the internal temperature reached 100° C. This cake was heated at 100° C. for 10 hr. After this time, the cake was triturated with hexane, broken up and subjected to filtration. The collected residue was suspended in hexane and the suspension was filtered. The process was repeated (5 times in all). Each time some ethyl acetate was added (to a final value of about 50%). The final resulting light brown solid (112.73 g) was dried in a vacuum desiccator under high vacuum (0.02 mm of Hg) to afford 85 g of crude product, i.e. the sodium salt of the title compound, which was used as such for subsequent reactions. The crude product had mp 195°–200° C. (dec); nmr (DMSO-d$_6$) 1.3 (t, J=7 Hz, 3H), 4.20 (q, J=7 Hz, 2H), 7.25 (m, 4H), 8.25 (d, J=10.5 Hz, 1H); ir (white mineral oil) 3500, 3430, 3230, 1675 cm$^{-1}$; uvλ-max (MeOH) 275 nm (ε17,915), 235 (12,380), 222 (11,725), shld at 300 nm.

EXAMPLE 2

3-Carboxy-1,2-dihydro-2-oxocyclohepta[b]pyrrole-1-acetic Acid (I, $R^1$, $R^2$ and $R^4$=H, $R^3$=COOH and X=O)

1,2-Dihydro-2-oxocyclohepta[b]pyrrole-3-carboxylic acid ethyl ester, sodium salt (50 g, described in example) was issolved in dry dimethyl sulfoxide (DMSO, 500 ml) to produce a dark homogeneous solution to which ethyl bromoacetate (25 ml) was added dropwise. The reaction mixture was stirred at room temperature for 30 hr. After this time, it was cooled to 0° C. in an ice/water bath and diluted with an equal volume of half-saturated brine (500 ml). The resulting precipitate was collected on a filter, washed with water and air dried to afford the crude product (30 g) as a yellow slightly sticky solid. This crude material was passed through a column of silica gel (500 g) and eluted stepwise using an ethyl acetate/hexane (1:1) mixture. Three fractions of two liters each were collected. Thereafter, the eluting solvent was changed to pure ethyl acetate and 3-(ethoxycarbonyl)-1,2-dihydro-2-oxocyclohepta[b]pyrrole-1-acetic acid ethyl ester (27.0 g) was obtained in fractions 4 to 8. This product was sufficiently pure for the following hydrolysis reaction. A sample recrystallized from ethyl acetate-hexane had mp 115°–120° C.; nmr (CDCl$_3$) $\delta$1.40 (m, 6H), 4.3 (m, 4H), 4.88 (s, 2H), 7.35 (m, 4H), 9.05 (d, 1H); ir (CHCl$_3$) 1741, 1717, 1672, 1604, 1589 cm$^{-1}$; uv$\lambda$max (MeOH) 420 nm ($\epsilon$15,480), 278 (30,165), 295 (17,120), 224 (17,880); Anal Calcd for C$_{16}$H$_{17}$NO$_5$: C, 63.36% H, 5.65% N, 4.62%; Found: C, 63.07% H, 5.80% N, 4.56%.

The latter was subjected to hydrolysis in the following manner: The compound (4.5 g) was suspended in 10% (w/v) aqueous NaOH (84 ml). The mixture was stirred at 25° C. After 16.5 hr, the mixture was cooled in an ice/water bath and treated with 10% (w/v) aqueous HCl (90 ml). The resulting precipitate was filtered quickly, washed briefly with cold water and allowed to dry under suction to afford the title compound: mp >250° C.; nmr (DMSO-d$_6$) $\delta$4.95 (s, 2H), 7.8 (m, 4H), 9.0 (d, J=10 Hz, 1H), 10.(broad s, 1H), 12.7 (broad, 1H); ir (white mineral oil) 2900, 1710, 1645 cm$^{-1}$; uv$\lambda$max (MeOH) 281 nm ($\epsilon$27,000), 230 (15,685), 220 (16,700); Anal Calcd for C$_{12}$H$_9$NO$_5$: C, 58.30% H, 3.67% N, 5.67%; Found: C, 57.87% H, 3.91% N, 5.55%.

EXAMPLE 3

1,2-Dihydro-2-oxocyclohepta[b]pyrrole-1-acetic Acid (I; R$^1$, R$^2$ and R$^4$=H, R$^3$=COOH and X=O)

A round bottomed flask, equipped with a magnetic stirrer, was charged with 3-carboxy-1,2-dihydro-2-oxocyclohepta[b]pyrrole-1-acetic acid (6.36 g, described in example 2). A solution of 10% (w/v) aqueous HCl (100 ml) was added. The resulting heterogeneous reaction mixture was stirred at 25° C. After 24 hr, the reaction mixture was filtered. The collected solid was air dried to give the title compound; mp 245° C. (dec); nmr (DMSO-d$_6$) $\delta$4.75 (s, 2H), 6.1 (s, 1H), 7.05 (m, 4H), 7.6 (d, J=10.8 Hz, 1H); ir (white mineral oil) 2500, 1970, 1705 and 1575 cm$^{-1}$; uv$\lambda$max (MeOH) 264 nm ($\epsilon$31,700); Anal Calcd for C$_{11}$H$_9$NO$_3$: C, 65.02% H, 4.46% N, 6.89%; Found: C, 64.53% H, 4.61% N, 6.82%.

EXAMPLE 4

3-(Ethoxycarbonyl)-1,2-dihydro-2-oxocyclohepta[b]pyrrole-1-acetic Acid (I; R$^1$, R$^2$ and R$^4$=H, R$^3$=COOC$_2$H$_5$ and X=O)

3-(Ethoxycarbonyl)-1,2-dihydro-2-oxocyclohepta[b]pyrrole-1-acetic acid ethyl ester (3.0 g, described in example 2) was suspended in ethanol (40 ml). An aqueous solution of 20% (w/v) of NaOH (2 ml) was added to the mixture. The mixture was stirred at 25° C. for 2 hr. A precipitate quickly formed. After the two hours, a check of the pH of the mixture showed it to be neutral. The mixture was evaporated to dryness at 25° C. The resulting solid was dissolved in water (50 ml). The pH of the solution was adjusted to 3 with dilute aqueous HCl and the solution was extracted with ethyl acetate. The extract was dried (Na$_2$SO$_4$), filtered and evaporated to dryness at room temperature to afford the title compound as a yellow solid. The compound, recrystallized once from ethyl acetate, had mp 215°–220° C.; nmr (DMSO-d$_6$) $\delta$1.3 (t, J=7 Hz, 3H), 4.25 (q, J=7 Hz, 2H), 4.85 (s, 2H), 7.6 (m, 4H), 8.85 (d, J=10.75 Hz, 1H); ir (white mineral oil) 2800, 1725, 1685, 1635 cm$^{-1}$; uv$\lambda$max (MeOH) 420 nm ($\epsilon$15,900), 285 (28,900), 232 (16,284), 221 (16,800).

EXAMPLE 5

3-Carboxy-1,2-dihydro-2-thioxocyclohepta[b]pyrrole-1-acetic Acid (I; R$^1$, R$^2$ and R$^4$=H, R$^3$=COOH and X=S)

3-(Ethoxycarbonyl)-1,2-dihydro-2-oxycyclohepta[b]pyrrole-1-acetic acid ethyl ester (6.0 g, described in example 2) was dissolved in pyridine (20 ml). Solid phosphorus pentasulfide (4.9 g) was added to the vigorously stirred solution. The mixture was immersed in an oil bath at 140° C. whereby it quickly became dark and homogeneous. The mixture was heated at reflux for 3 hr, cooled and poured into 200 ml of warm water (about 45° C.). The mixture was stirred for 20 min. During this time, the dark tarry oil which was initially produced on contact with water began to solidify. After this time the mixture was cooled to 0° C. for 30 min. The resulting precipitate was collected on a filter to give 5.5 g of crude product. The aqueous filtrate was extracted (3×100 ml) with methylene chloride. The combined organic phase was dried (Na$_2$—SO$_4$) and filtered. The filtered organic phase was evaporated to afford a further amount (2.3 g) of the crude product. The two crude products were combind and again subjected to the above treatment with phosphorous pentasulfide. The resulting product was purified by chromatography on silica gel using ethyl acetate-hexane (1:1) as the eluant. The pure fractions were pooled to give 3-(ethoxycarbonyl)-1,2-dihydro-2-thioxocyclohepta[b]pyrrole-1-acetic acid ethyl ester; nmr (CDCl$_3$) $\delta$1.25 (t, J=7 Hz, 3H), 1.45 (t, J=7 Hz, 3H), 4.45 (q, J=7 Hz, 2), 4.2 (q, J=7 Hz, 2H), 5.43 (s, 2H), 7.4 (m, 4H), 8.6 (d, J=11 Hz, 1H); ir (CHCl$_3$) 1742, 1710, 1682 cm$^{-1}$.

The latter compound was hydrolyzed by mixing the compound (1.7 g) with water (17 ml) and 20% (w/v) aqueous NaOH (17 ml), and stirring the mixture for 16 hrs at 25° C. The mixture was extracted with diethyl ether. The aqueous phase was diluted to 125 ml with water, cooled to 0° C. and made acidic with 10% (w/v) aqueous HCl. The precipitate was collected and dried in a vacuum desiccator over NaOH to afford a crude product (1.89 g, mp 240°–243° C.). The crude product was boiled in ethyl acetate (30 ml) and collected on a filter. The latter process was repeated twice more to give 1.37 g of the title compound; mp 240°–250° C.; nmr (DMSO-d$_6$) $\delta$6.45 (s, 2H), 8.15 (m, 4H), 9.5 (m, 1H); uv$\lambda$max (MeOH) 282 nm (18,110), 220 (16,695); ir (white mineral oil) 2900, 1730, 1690, 1650 cm$^{-1}$; Anal Calcd for C$_{12}$H$_9$NO$_4$S: C, 54.75% H, 3.45% N, 5.32%; Found: C, 53.69% H, 3.63% N, 4.74%.

EXAMPLE 6

1,2-Dihydro-3-[(2,2-dimethyl-1-oxopropoxy)methoxycarbonyl]-2-oxo-cyclohepta[b]pyrrole-1-acetic Acid (2,2-Dimethyl-1-oxopropoxy)methyl Ester (I; R$^1$ and R$^4$=H, R$^2$=CH$_2$OCOC(CH$_3$)$_3$, R$^3$=COOCH$_2$OCOC(CH$_3$)$_3$ and X=O)

3-Carboxy-1,2-dihydro-2-oxocyclohepta[b]pyrrole-3-carboxylic acid (620 mg, described in example 2) was dissolved in DMSO (10 ml). Potassium carbonate (1.38 g), 2,2dimethylpropionic acid chloromethyl ester (0.6 ml) and potassium iodide (50 mg) were added. The resulting mixture was stirred at 22° C. for 18 hr. The reaction mixture was cooled to 0° C. and mixed with brine (10 ml). Solid material in the mixture was collected on a filter and washed with water (3×15 ml). The solid material was dissolved in ethyl acetate and the solution filtered. The organic filtrate was dried ($Na_2SO_4$) and evaporated to dryness to give 1.0 g of a brown foam. The foam was subjected to chromatography on silica gel (25 g) using ethyl acetate-hexane (3:2) as the eluant. The pure fractions were pooled and the resulting yellow foam was crystallized from ethyl acetate-hexane to give 0.55 g of the title compound; mp 110°–112° C.; nmr ($CDCl_3$) δ1.15 & 1.2 (s, 13H), 4.9 (s, 2H), 5.75 (s, 2H), 6.0 (s, 2H), 7.4 (m, 5H); ir ($CHCl_3$) 1740, 1692 cm$^{-1}$; uvλmax (MeOH) 279 nm (ε29,000), 234 (17,000), 226 (17,000); Anal Calcd for $C_{24}H_{29}NO_6$: C, 60.62% H, 6.15% N, 2.95%; Found: C, 60.77% H, 6.19% N, 2.97%.

EXAMPLE 7

3-Acetyl-1,2-dihydro-2-oxocyclohepta[b]pyrrole-1-acetic Acid (I; $R^1$, $R^2$ and $R^4$=H, $R^3$=$COCH_3$ and X=O)

To a warm suspension of 3-acetyl-1,2-dihydrocyclohepta[b]pyrrole-2-one [1.87 g, described by T. Nozoe et al., Bull. Chem. Soc. Japan, 38, 306 (1965)] in dimethyl formamide (DMF, 25 ml), potassium carbonate (1.66 g) and ethyl bromoacetate (2.84) were added successively. The mixture was stirred at 25° C. for 18 hr and then diluted with water. The precipitate was collected and dried to give 3-acetyl-1,2-dihydro-2-oxocyclohepta[b]pyrrole-1-acetic acid ethyl ester, mp 162°–165° C.; nmr ($CDCl_3$) δ1.33 (t, J=7 Hz, 3H), 2.75 (s, 3H), 4.25 (q, J=7 Hz, 2H), 4.9 (s, 2H), 7.4 (m, 4H), 9.4 (d, J=10 Hz, 1H).

The latter compound (1.99 g) was suspended in methanol (15 ml). A solution of NaOH (0.32 g) in methanol (4 ml) was added to the suspension. The mixture was stirred for 20 min., diluted with water and rendered acidic by the addition of 10% (w/v) aqueous HCl (3 ml). The precipitate was collected and dried to give 1.66 g of the title compound; mp 252°–254° C. (after two recrystallizations from methanol-diethyl ether); nmr (DMSO-$d_6$) δ2.53 (s, 3H), 4.87 (s, 2H), 7.72 (m, 3H), 9.25 (d, J=10 Hz, 1H); ir (white mineral oil) 2500, 1742, 1724, 1671 cm$^{-1}$; Anal Calcd for $C_{13}H_{11}NO_4$: C, 63.67% H, 4.52% N, 5.71%; Found: C, 64.21% H, 4.47% N, 5.66%.

EXAMPLE 8

3-Ethyl-1,2-dihydro-2-oxocyclohepta[b]pyrrole-1-acetic Acid (I; $R^1$, $R^2$ and $R^4$=H, $R^3$=$C_2H_5$ and X=O)

3-Acetyl-1,2-dihydrocyclohepta[b]pyrrol-2-one (5.6 g) was suspended in methanol (15 ml). A saturated solution of dry HCl in diethyl ether (10 ml) was added to the suspension. Sodium cyanoborohydride (11.3 g) was gradually added to the suspension which was maintained acidic by the simultaneous addition of more of the HCl solution. The reaction mixture was diluted with a saturated solution of NaCl in water and extracted with ethyl acetate. The extract was dried ($Na_2SO_4$) and evaporated to dryness. The residue was dissolved in chloroform and poured through a column of silica gel. Elution of the column with chloroform-methanol (98:2) gave 3-ethyl-1,2-dihydrocyclohepta[b]pyrrol-2-one; mp 166°–171° C.; nmr ($CDCl_3$) δ1.2 (t, J=7 Hz, 3H), 2.65 (q, J=7 Hz, 2H), 7.1 (m, 5H), 12.0 (s, 1H).

The latter compound (2.7 g) was dissolved in DMSO (12 ml). Potassium carbonate (2.6 g) was added to the solution, followed by the addition of ethyl bromoacetate (4.4 g). The mixture was stirred at 25° C. for 72 hr, heated at 75° C. for 2 hr, cooled, diluted with water and extracted with ethyl acetate. The extract was dried ($Na_2SO_4$), filtered and evaporated to dryness. The residue was dissolved in ethyl acetate-hexane (1:1) and the solution poured through a column of silica gel. The eluate was concentrated to dryness to give 3-ethyl-2-oxocyclohepta[b]pyrrole-1-acetic acid ethyl ester; mp 128°–131° C.; nmr ($CDCl_3$) δ1.3 (t, J=7 Hz, 3H), 2.7 (q, J=7 Hz, 2H), 4.25 (q, 2H), 4.85 (s, 2H), 6.8 (m, 5H); ir ($CHCl_3$) 1700, 1740 cm$^{-1}$; Anal Calcd for $C_{15}H_{17}NO_3$: C, 69.48% H, 6.61% N, 5.40%; Found: C, 69.34% H, 6.68% N, 5.44%.

The latter compound (2.4 g) was suspended in ethanol (20 ml). A solution of NaOH (0.407 g) in ethanol-water (1:1, 20 ml) was added to the suspension. The solid dissolved and then after 30 min a precipitate had formed. The precipitate dissolved on the addition of water to the reaction mixture. The mixture was made acidic by the addition of concentrated HCl. The resulting precipitate was collected and dried to yield 2.1 g of the title compound, mp 260°–262° C. Recrystallization of the compound gave an analytical sample; mp 258°–262° C.; nmr (DMSO-$d_6$) δ1.08 (q,J=HHz, 3H), 2.54 (q,J=7 Hz, 2H), 4.75 (s,2H), 6.98 (m, 3H), 7.48 (d, 2H); ir (white mineral oil) 2500, 1730, 1604, 1585 cm$^{-1}$; uvλmax(MeOH) 270 nm (ε34,385); Anal Calcd for $C_{13}H_{13}NO_3$: C, 67.52% H, 5.67% N, 6.06%; Found: C, 67.46% H, 5.67% N, 6.16%.

EXAMPLE 9

3-Carboxy-6-chloro-1,2-dihydro-2-oxocyclohepta[b]pyrrole-1-acetic Acid (I; $R^1$ and $R^2$=H, $R^3$=COOH, $R^4$=6-Cl and X=O)

5-Chlorotropolone [40 g, described by T. Nozoe et al., Proc. Japan Acad., 27,4 (1951)], dimethyl sulfate (60 ml), anhydrous potassium carbonate (40 g) and 2-butanone (550 ml) were heated at reflux for 1.5 hr. The cooled reaction mixture was filtered and the filtrate was evaporated to dryness. The residue was triturated with diethyl ether and 5-chloro-2-methoxy-2,4,6-cycloheptatrien-1-one, mp 124°–126° C.; nmr ($CDCl_3$) δ3.9 (s, 3H), 7.0 (m, 4H), was isolated by filtration. The residue obtained by evaporation of the filtrate, was purified by column chromatography over silica gel using chloroform-methanol (49:1) as the eluant. Pooling of the appropriate fractions gave another 2.6 g of 5-chloro-2-methoxy-2,4,6-cycloheptatrien-1-one.

The latter compound (5g) was dissolved in methanol (100 ml) saturated with anhydrous ammonia. The mixture was heated in a pressure bottle at 80° C. for one hr. The mixture was evaporated to dryness and the residue was purified by chromatography on silica gel using chloroform-methanol (19:1) as the eluant. The appropriate fractions were pooled to give 4.07 g of 2-amino-5-chloro-2,4,6-cycloheptatrien-1-one, nmr (DMSO-$d_6$) δ6.8 and 7.35 (2d, 4H), 7.65 (broad,2H).

The latter compound (15.5 g) was added in one portion to a stirred mixture of sodium hydride (5.0 g, 5% suspension in mineral oil) and diethyl malonate (35 ml) cooled in an ice-bath. The mixture of sodium hydride and diethyl malonate had been prepared by carefully adding the sodium hydride suspension to cooled diethyl malonate. An additional 15 ml of diethyl malonate was added to the reaction mixture. The mixture was heated at 130° C. for 30 min., cooled, diluted with water and extracted with chloroform. The aqueous phase was rendered acidic with 6 N aqueous HCl. The resulting precipitate was collected and dried to give 8.1 g of the intermediate, 6-chloro-1,2-dihydro-2-oxocyclohepta[b]pyrrole-3-carboxylic acid ethyl ester. An additional 1.0 g of the product was obtained by purifying the residue from the chloroform extract by chromatography on silica gel using chloroform-methanol (97:3) as the eluate. The ethyl ester had mp 218°–220° C.; nmr (DMSO-$d_6$) δ1.3 (t, 3H), 4.25 (q,2H), 7.25 (d, 1H), 7.75 (m, 2H), 8.55 (d, 1H); ir (white mineral oil) 2850, 1680 cm$^{-1}$; uvλmax (CH$_3$OH) 276 nm (ε28,310), 224 (18,340); Anal Calcd for $C_{12}H_{10}ClNO_3$: C, 57.27% H, 4.01% N, 5.57%; Found: C, 57.02% H, 3.98% N, 5.54%. T. Nozoe et al., Japanese Pat. No. 2217/57, Apr. 11, 1957 reports that the compound has mp 225° C., see Chem. Abstr., 52, 64 11e (1958).

The latter intermediate (7 g) was alkylated with ethyl bromoacetate (7 ml) and potassium carbonate (20 g) in DMF (150 ml) in the manner described in example 7 to give 6-chloro-3-(ethoxycarbonyl)-1,2-dihydro-2-oxocyclohepta-[b]pyrrole-1-acetic acid ethyl ester (7.7 g) mp 177°–179° C. (after recrystallization from acetone); nmr (CDCl$_3$) δ1.3 (m, 6H), 4.25 (m, 4H), 4.8 (s, 2H), 7.15 (m, 3H), 8.85 (d, 1H); ir (white mineral oil) 1730, 1700, 1680 cm$^{-1}$; uvλmax (MeOH) 283 nm (ε32,410), 225 (18,085); Anal Calcd for $C_{16}H_{16}ClNO_5$: C, 56.90% H, 4.78% N, 4.15%; Found: C, 56.93% H, 4.77% N, 4.14%.

Hydrolysis of the latter compound (1.5 g) in a suspension of 2 N aqueous NaOH in the manner described in example 2 gave the title compound (1.0 g); mp 250° C.; nmr (DMSO-$d_6$) δ4.90 (s, 2H), 7.7 (m, 3H), 8.75 (d, 1H); ir (white mineral oil) 2900, 1720, 1655 cm$^{-1}$; uvλmax (MeOH) 286 nm (ε28,535), 223 (17,645); Anal Calcd for $C_{12}H_8ClNO_5$: C, 51.17% H, 2.86% N, 4.97%; Found: C, 51.73% H, 2.99% N, 4.99%.

EXAMPLE 10

6-Chloro-3-(ethoxycarbonyl)-1,2-dihydro-2-oxocyclohepta[b]pyrrole-1-acetic Acid (I;$R^1$ and $R^2$=H, $R^3$=COOC$_2$H$_5$, $R^4$=6-Cl and X=O)

A mixture of 6-chloro-3-(ethoxycarbonyl)-1,2-dihydro-2-oxocyclohepta[b]pyrrole-1-acetic acid ethyl ester (2 g, described in example 9), ethanol (40 ml) and 2 N aqueous NaOH (10 ml) was stirred at 25° C. for 2 hr. The mixture was diluted with water and extracted with chloroform. The aqueous phase was made acidic. The resulting precipitate was collected on a filter, dried and recrystallized from methanol to give the title compound (1.8 g); mp >250° C.; nmr (DMSO-$d_6$) δ1.3 (t, 3H), 4.25 (q, 2H), 4.85 (s, 2H), 7.65 (m, 3H), 8.75 (d, 1H); ir (white mineral oil) 2900, 1743, 1685, 1660 cm$^{-1}$; uvλmax (MeOH) 285 nm (ε30,465), 225 (16,755); Anal Calcd for $C_{14}H_{12}ClNO_5$: C, 54.29% H, 3.91N, 4.52%; Found: C, 53.70% H, 3.88% N, 4.54%.

EXAMPLE 11

3-Acetyl-6-chloro-1,2-dihydro-2-oxocyclohepta[b]pyrrole-1-acetic Acid (I; $R^1$ and $R^2$=H,$R^3$=COCH$_3$, $R^4$=6-Cl and X=O)

A mixture of 2-amino-5-chloro-2,4,6-cycloheptatrien-1-one (1.55 g, described in example 9) and diketene (5 ml) were heated at 100° C. for 1 hr. The mixture was cooled and then purified by chromatography on silica gel using chloroform as the eluant. The appropriate fractions were pooled and the residue was crystallized from diethyl ether to give 650 mg of 1-[(4-chloro-7-oxo-1,3,5-cycloheptatrien-1-yl)amino]-1,3-butanedione, nmr (DMSO-$d_6$) δ2.17 (s, 3H), 3.85 (s, 2H), 7.3 (m, 3H), 8.7 (d, 1H), 10.75 (s, 1H).

The latter compound can be converted to 3-acetyl-6-chloro-1,2-dihydro-2-ococyclo[b]pyrrole-1-acetic acid ethyl ester by either of the following methods A or B:

Method A: 1-[(4-Chloro-7-oxo-1,3,5-cycloheptatrien-1-yl)amino]-1,3-butanedione (480 mg) was suspended in a solution of sodium ethoxide (prepared from 46 mg of sodium and 2 ml of anhydrous ethanol). The solution was heated at reflux for 3 hr. The reaction mixture was cooled and filtered. The filtrate was evaporated to dryness. The residue was dissolved in water. The solution was rendered acidic with 6 N aqueous HCl. The precipitate was collected and dried to give 3-acetyl-6-chloro-1,2-dihydro-2-oxocyclohepta[b]pyrrole, nmr (DMSO-$d_6$) δ2.55 (s, 3H), 7.3–7.95 (m, 3H), 8.9 (d, 1H). The latter compound (5.8 g) was added to a stirred solution of sodium hydride (77 mg, 50% suspension in mineral oil) and DMF (10 ml), the solution having been stirred at 25° C. for 30 min prior to the addition. Thereafter, ethyl bromoacetate (400 mg) was added to the mixture. The mixture was heated at 100°–105° C. for 1.5 hr, cooled, diluted with water and extracted with chloroform. The residue was purified by chromatography on silica gel using methylene chloride-ethyl acetate (9:1) as the eluant. The pure fractions were pooled to give 3-acetyl-6-chloro-1,2-dihydro-2-oxocyclohepta[b]pyrrole-1-acetic acid ethyl ester, nmr (CDCl$_3$) δ1.3 (t, 3H), 2.7 (s, 3H), 4.2 (q, 2H), 4.85 (s, 2H), 7.6 (m, 4H).

Method B: A mixture of 1-[(4-chloro-7-oxo-1,3,5-cycloheptatrien-1-yl)amino]-1,3-butanedione (5.8 g) and sodium ethoxide solution, prepared by dissolving 1.1 g of sodium in 200 ml of anhydrous, methanol-free ethanol, was heated at reflux for 5 hr. Thereafter, ethyl bromoacetate (10 ml) was added dropwise to the hot solution and refluxing was continued for an additional 10 min. The reaction mixture was evaporated to dryness. The residue was dissolved in chloroform and the solution filtered through a column of silica gel. Evaporation of the eluate gave 3.75 g of 3-acetyl-6-chloro-1,2-dihydro-2-oxocyclohepta[b]pyrrole-1-acetic acid ethyl ester, identical to the compound obtained from method A. Crystallization of the latter compound gave the product with mp 183.5° C.; nmr (CDCl$_3$) δ1.27 (t, 3H), 2.7 (s, 3H), 4.2 (q, 2H), 4.85 (s, 2H), 6.85–9.3 (m, 4H); ir (white mineral oil) 1725, 1685 cm$^{-1}$; uvλmax (MeOH) 293 nm (ε21,995), 256 (14,630), 231 (16,945); Anal Calcd for $C_{15}H_{14}ClNO_4$: C, 58.55% H, 4.59% N, 4.55%; Found: C, 58.53% H, 4.60% N, 4.54%.

A mixture of the latter compound (0.6 g) in 15% (w/v) aqueous HCl (25 ml) was heated at reflux for 1.5 hr and then cooled. The resulting precipitate was collected and washed with acetone to give 450 mg of the title compound; mp 273°–275° C.; nmr (DMSO-$d_6$) δ2.55 (s, 3H), 4.85 (s, 2H), 7.8 (m, 3H), 9.05 (d, 1H); ir (white mineral oil) 2800, 1755, 1680 cm$^{-1}$; uvλmax (MeOH)297 nm (ε27,505), 257 (14,475), 228 (16,615), 211 (19,310); Anal Calcd for $C_{13}H_{10}ClNO_4$: C, 55.83% H, 3.66% N, 5.01%; Found: C, 55.97% H, 3.66% N, 5.11%.

EXAMPLE 12

3-Cyano-1,2-dihydro-2-oxocyclohepta[b]pyrrole-1-acetic Acid (I; $R^1$, $R^2$ and $R^4$=H, $R^3$=CN and X=O)

A 1 N solution of sodium methoxide in methanol (100 ml) was added to a solution of 2-methoxy-2,4,6-cycloheptatrien-1-one (13.6 g), see F. Pietra, Chem. Rev., 73, 293 (1973) and references therein, and 2-cyanoacetamide (8.4 g) in 50 ml of ethanol. The reaction mixture was stirred in a sealed vessel at 25° C. for 5 hrs. The reaction mixture was filtered into a second vessel and the collected material on the filter was washed with ethanol. To the combined filtrate and washings, ethyl bromoacetate (11 ml) was added. The vessel holding the mixture was sealed and the mixture was stirred at 25° C. for 18 hr. Thereafter, the solvent was removed by distillation under reduced pressure. The residue was triturated with methylene chloride and the mixture was filtered. The collected solids (inorganic salts) were washed with additional methylene chloride. The combined filtrate and washings were concentrated to dryness. The residue was purified by chromatography on silica gel (750 g) using ethyl acetate as the eluant. The pure fractions were pooled and the residue was crystallized from ethyl acetate-hexane to give 3-cyano-1,2-dihydro-2-oxocyclohepta[b]pyrrole-1-acetic acid ethyl ester; mp 149°–151° C., nmr (CDCl$_3$) $\delta$1.25 (t, J=7 Hz, 3H), 4.15 (q, J=7 Hz, 2H), 4.8 (s, 2H), 7.5 (m, 5H); ir (CHCl$_{3;L}$) 2220, 1745, 1695 cm$^{-1}$; uv$\lambda$max (MeOH) 275 nm ($\epsilon$31,900), 217 (18,100); Anal Calcd for $C_{14}H_{12}N_2O_3$: C, 65.62% H, 4.72% N, 10.93%; Found: C, 65.37% H, 4.74% N, 16.95%.

The latter compound was hydrolyzed as follows. The compound (2.27 g) was suspended in water (17 ml). 20% (w/v) aqueous HCl (2 ml) was added to the suspension. The suspension was stirred at 25° C. for 16 hr. The mixture was extracted with methylene chloride. The aqueous phase was made acidic with concentrated HCl. The resulting precipitate was collected, washed with water and air dried to give 2.0 g of the title compound; mp 294°–295° C.; nmr (DMSO-d$_6$) $\delta$4.85 (s, 2H), 7.7 (m, 6H), uv$\lambda$max (MeOH) 2.78 nm ($\epsilon$29,500), 216 (16,700); ir (white mineral oil) 3000, 2220, 1735, 1660 cm$^{-1}$; Anal Calcd for $C_{12}H_8N_2O_3$: C, 63.16% H, 3.53% N, 12.28%; Found: C, 62.89% H, 3.67% N, 12.02%.

EXAMPLE 13

3-(Aminocarbonyl)-1,2-dihydro-2-oxocyclohepta[b]pyrrole-1-acetic Acid (I; $R^1$, $R^2$ and $R^4$=H, $R^3$=CONH$_2$ and X=O)

3-Cyano-1,2-dihydro-2-oxocyclohepta[b]pyrrole-1-acetic acid ethyl ester (2.56 g, described in example 12), was suspended in concentrated H$_2$SO$_4$ (10 ml). The mixture was stirred at 25° C. for 3 hr and then poured into ice water (20 ml). After 5 minutes, the resulting solid was collected on a filter, washed with water and then diethyl ether, air dried and recrystallized from ethanol diethyl ether to give 1.75 g of 3-(aminocarbonyl)-1,2-dihydro-2-oxocyclohepta[b]pyrrole-1-acetic acid ethyl ester; mp 215°–220° C.; nmr (DMSO-d$_6$) $\delta$1.20 (t, J=7.5 Hz, 3H), 3.25 (broad, 2H), 4.15 (q, J=7.5 Hz, 2H), 5.0 (s, 2H), 7.6 (m, 4H), 9.3 (d, J=10 Hz, 1H); ir (white mineral oil) 3360, 3160, 1743, 1734, 1667, 1590 cm$^{-1}$; uv$\lambda$max (MeOH) 276 nm ($\epsilon$32,100), 232 (17,200), 223 (17,100); Anal Calc for $C_{14}H_{14}N_2O_4$: C, 61.36% H, 5.15% N, 10.21%; Found: C, 61.12% H, 5.26% N, 10.24%.

The latter compound (500 mg) was hydrolyzed with 20% (w/v) aqueous NaOH (1 ml) under the same conditions as described for the hydrolysis in example 2 to give the title compound: mp>275° C.; nmr (DMSO-d$_6$) $\delta$4.90 (s, 2H), 7.6 (m, 4H), 7.30 and 8.00 (broad, 2H), 8.35 (broad, 1H), 9.3 (d, J=10 Hz, 1H); ir (white mineral oil) 3350, 3190, 1755, 1700, 1675, 1625 cm$^{-1}$; uv$\lambda$max (MeOH) 278 nm ($\epsilon$30,000), 231 (16,100), 224 (16,000); Anal Calcd for $C_{12}H_{10}N_2O_4$: C, 58.21% H, 4.12% N, 11.31%; Found: C, 58.19% H, 4.18% N, 11.24%.

EXAMPLE 14

2-(3-Carboxy-1,2-dihydro-2-oxocyclohepta[b]pyrrol-1-yl)butanedioic Acid (I; $R^1$=CH$_2$COOH, $R^2$ and $R^4$=H, $R^3$=COOH and X=O)

A mixture of 1,2-dihydro-2-oxocyclohepta[b]pyrrole-3-carboxylic acid ethyl ester, sodium salt (12.5 g, described in example 1) and 2-bromobutanedioic acid dimethyl ester (14.5 g) in DMF (14.5 g) was heated at 100° C. for 48 hr. The mixture was cooled, diluted with water and extracted with chloroform. The chloroform extract was passed through a column of silica gel. Subsequent elution of the column with chloroform-methanol (97:3) gave 2.0 g of 2-(3-ethoxycarbonyl-1,2-dihydro-2-oxocyclohepta[b]pyrrol-1-yl) butanedioic acid dimethyl ester, nmr (CDCl$_3$) $\delta$1.4 (t, 3H), 3.35 (m, 2H), 3.6 and 3.7 (2s, 6H), 4.4 (q, 2H), 5.6 (t, 1H), 7.45 (m, 4H), 9.05 (d, 1H).

The latter compound was hydrolyzed as follows. The compound (1.8 g) was suspended in 2 N aqueous NaOH (20 ml) and methanol (5 ml). The suspension was heated at 80° C. for 15 min., cooled and extracted with chloroform. The aqueous phase was made acidic with concentrated HCl. The resulting precipitate was collected on a filter, washed with water and dried under reduced pressure to give 1.4 g of the title compound; mp 219°–220° C. (dec); nmr (DMSO-d$_6$) $\delta$3.2 (m, 2H), 5.84 (t, 1H), 7.75 (m, 4H), 8.0 (d, 1H); ir (white mineral oil) 3000, 1730, 1674, 1620 cm$^{-1}$; uv$\lambda$max (MeOH) 280 nm ($\epsilon$27,600), 231 (17,170), 221 (18,090); Anal Calcd for $C_{14}H_{11}NO_7$: C, 55.09% H, 3.63% N, 4.59%; Found: C, 55.24% H, 3.72% N, 4.66%.

EXAMPLE 15

6-Chloro-3-[(N-carboxymethyl-N-methyl)amino]carbonyl-1,2-dihydro-2-oxocyclohepta[b]pyrrole-1-acetic Acid (I: $R^1$ and $R^2$=H, $R^3$=CON(CH$_3$)CH$_2$COOH, $R^4$=Cl and X=O)

6-Chloro-1,2-dihydro-2-oxocyclohepta[b]pyrrole-3-carboxylic acid ethyl ester (1.0 g, described in example 9) was hydrolyzed with 2 N aqueous NaOH (20 ml) under the conditions described for the hydrolysis in example 14 to give 6-chloro-1,2-dihydro-2-oxocyclohepta[b]pyrrole-3-carboxylic acid; mp 227° C. (dec); nmr (DMSO-d$_6$) $\delta$7.39-9.8 (m, 4H), 12.4 (s, 2H).

The latter compound (2.6 g) was heated at reflux with thionyl chloride (30 ml) for 15 min. The solution was evaporated to dryness. The residue (i.e. the corresponding acid chloride) was dissolved in benzene and the solution was evaporated to dryness to remove traces of thionyl chloride. A suspension of N-methylglycine methyl ester hydrochloride (8 g) in pyridine (50 ml) was added to the acid chloride. The reaction mixture was kept at 25° C. for 2 hr and then at 70°-80° C. for 10 min. The mixture was diluted with water and extracted with chloroform. The organic extract was evaporated to dryness. The residue was purified by chromatography on silica gel using chloroform-methanol (95:5) as the eluant. The fractions were pooled to give N-[(6-chloro-1,2-dihydro-2-oxocyclohepta[b]pyrrole-3-yl)carbonyl]-N-methylglycine methyl ester: mp 170°–172° C.; nmr (CDCl$_3$) δ3.17 (s, 3H), 3.62 and 3.78 (d, 3H), 4.27 (s, 2H), 7.35 (m, 3H), 8.0 (m, 3H), 10.9 (s, 1H).

The latter compound (1.6 g) was alkylated with ethyl bromoacetate (2 g) and potassium carbonate (2 g) in DMF (60 ml) at 25° C. for 3 hr. Thereafter, the reaction mixture was diluted with water and extracted with chloroform. The extract was evaporated to dryness. The residue was purified by chromatography on silica gel using chloroform-methanol (99:1) as the eluant. The pure fractions were pooled to give 1.7 g of 6-chloro-3{[(N-ethoxycarbonylmethyl-N-methyl)amino]carbonyl}-1,2-dihydro-2-oxocyclohepta[b]pyrrole-1-acetic acid ethyl ester; nmr (CDCl$_3$) δ1.23 (t, 3H), 3.11 (s, 3H), 3.7 (broad, 3H), 4.18 (q, 2H), 4.23 (s, 2H), 4.77 (s, 2H), 6.77 (d, 1H), 7.30 (m, 2H), 7.95 (m, 1H), ir (CHCl$_3$) 1740, 1765 cm$^{-1}$; uvλmax (MeOH) 280 nm (ε25,600), 228 (12,360).

A suspension of the latter compound (1.65 g) in 2% (w/v), aqueous NaOH (17 ml) was stirred at 25° C. for 20 hr. The clear solution was evaporated to dryness. The crude product was crystallized from water to give 0.9 g of the title compound in the form of its disodium salt, mp >250° C.; nmr (D$_2$O) 3.1 (broad, 3H), 4.0 (broad, 3H), 7.0–8.1 (m, 4H); ir (KBr) 1630 cm$^{-1}$. The salt was hydroscopic.

EXAMPLE 16

3-Carboxy-1-(carboxymethyl)-cyclohepta[b]pyrrolium Chloride

A mixture of 2-amino-2,4,6-cycloheptatrien-1-one [2 g, described by W. Von E. Doering and L. H. Knox, J. Amer. Chem. Soc., 73, 828 (1951)] and diethyl ethoxymethylenemalonate (20 ml) was heated at 140° C. for 2 hr. The reaction was cooled and subjected to chromatography on silica gel using methylene chloride-ethyl acetate (4:1) as the eluant. The pure fractions were pooled to give 4.13 g of 2-[(7-oxo-1,3,5-cycloheptatrien-1-yl)aminomethylene]-propanedioic acid diethyl ester; mp 66°–68° C.; nmr (CDCl$_3$) δ1.35 (m, 6H), 4.35 (m, 2H), 7.35 (m, 5H), 8.4 (d, 1H), 11.4 (broad, 1H); ir (CHCl$_3$) 3230, 1700, 1665, 1580 cm$^{-1}$; uvλmax (MeOH) 356 nm (ε13,770), 292 (9,880), 277 (10,680), 213 (17,020) with shoulders at 338 and 236 nm.

The latter compound (5 g) was added to 100 ml of boiling diphenyl ether. After 10 minutes, the reaction mixture was cooled and diluted with chloroform. Thin layer chromatography on silica gel plates using chloroform-methanol (19:1) as the mobile phase indicated two main products (Rf 0.6 and Rf 0.5). The same thermal cyclization was repeated with three more 5 g portions. The pooled reaction mixtures were subjected to chromatography on silica gel using chloroformmethanol (99:1) as the eluant. The two main products thus were separated. The product with Rf 0.6 (7.2 g) was identified as cyclohepta[b]pyrrolo-3-carboxylic acid ethyl ester; mp 65°–67° C.; nmr (CDCl$_3$) δ1.4 (t, 3H), 4.4 (q, 2H), 7.8–9.6 (m, 6H). The byproduct with Rf 0.5 (4.7 g, after recrystallization from ethanol) was identified as 4,9-dihydro-4,9-dioxo-1H-cyclohepta[b]pyridine-3-carboxylic acid ethyl ester; mp 188°–190° C.; nmr (CDCl$_3$) δ1.4 (t, 3H), 4.4 (q, 2H), 7.0–8.7 (m, 6H), ir (white mineral oil) 3100, 1717 cm$^{-1}$.

A mixture of the above product (3.0 g, Rf 0.6), ethyl bromoacetate (12 ml) and dioxane (80 ml) was stirred at 25° C. for 48 hr. The precipitate was collected by filtration and triturated with methylene chloride to yield 4.2 g of 3-carboxyl-1-(carboethoxymethyl)-cyclohepta[b]pyrrolium bromide; mp >250° C.; nmr (DMSO-d$_6$) δ1.3 (m, 6H), 4.3 (m, 4H), 5.85 (s, 2H), 9.5 (m, 6H); ir (white mineral oil) 1735, 1715 cm$^{-1}$; uvλmax (MeOH) 307 nm (ε6,400) 273 (35,500), 217 (25,500).

A mixture of the latter compound (2.8 g) and 10% (w/v) aqueous HCl (50 ml) was heated at reflux for 3 hr. The solution was evaporated to dryness. The residue was crystallized from water-acetone to give 1.8 g of the title compound; mp >250° C.; nmr (DMSO-d$_6$) δ5.8 (s, 2H), 8.9 (m, 3H), 9.45 (m, 2H), 10.1 (m, 1H); ir (white mineral oil) 2900, 1740, 1710 cm$^{-1}$; uvλmax (MeOH) 306 nm (ε5,350), 275 (26,900), 217 (22,500); Anal Calcd for C$_{12}$H$_{10}$ClNO$_4$: C, 53.85% H, 3.77% N, 5.23%; Found: C, 54.86% H, 4.12% N, 5.35%.

We claim:

1. A compound of formula I

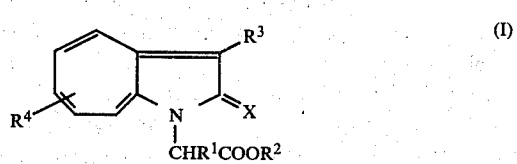

(I)

in which R$^1$ is hydrogen, carboxymethyl or lower alkoxycarbonylmethyl; R$^2$ is hydrogen, lower alkyl or (2,2-dimethyl-1-oxopropoxy)methyl; R$^3$ is hydrogen, lower alkyl, 1-oxo(lower)alkyl, carboxy, lower alkoxycarbonyl, (2,2-dimethyl-1-oxopropoxy)methoxycarbonyl, cyano, aminocarbonyl or CON(R$^5$)CH$_2$COOR$^6$ wherein R$^5$ is lower alkyl and R$^6$ is hydrogen or lower alkyl; R$^4$ is hydrogen, lower alkyl, lower alkoxy or halo; and X is oxo or thioxo; with the provisos that when R$^1$ is carboxymethyl then R$^2$ is hydrogen, that when R$^1$ is lower alkoxycarbonylmethyl then R$^2$ is lower alkyl, that when R$^2$ is (2,2-dimethyl-1-oxopropoxy)methyl then R$^1$ is hydrogen and R$^3$ is (2,2-dimethyl-1-oxopropoxy)methoxycarbonyl, that when R$^6$ is hydrogen then R$^1$ is hydrogen or carboxymethyl and R$^2$ is hydrogen, that when R$^6$ is lower alkyl then R$^1$ is hydrogen or lower alkoxycarbonylmethyl and R$^2$ is lower alkyl, that when R$^3$ is hydrogen then R$^1$ is hydrogen or carboxymethyl and R$^2$ is hydrogen, and that when X is thio then R$^1$ is hydrogen, R$^2$ is hydrogen, lower alkyl or (2,2-dimethyl-1-oxopropoxy)methyl, and R$^3$ is carboxy, lower alkoxycarbonyl or (2,2-dimethyl-1-oxopropoxy)-methoxycarbonyl; or a therapeutically acceptable salt, with an organic or inorganic base, of the compounds of formula I having one or more carboxyls.

2. The compound of formula I, as claimed in claim 1, in which R$^1$ is hydrogen, carboxymethyl, methoxycarbonylmethyl or ethoxycarbonylmethyl; R$^2$ is hydrogen, methyl, ethyl or (2,2-dimethyl-1-oxopropoxy)methyl; R$^3$ is hydrogen, methyl, ethyl, acetyl, carboxy, methoxycarbonyl, ethoxycarbonyl, (2,2-dimethyl-1-oxopropoxy)methoxycarbonyl, cyano, aminocarbonyl or CON(CH$_3$)CH$_2$COOR$^6$ wherein R$^6$ is hydrogen, methyl or ethyl; R$^4$ is hydrogen or chloro and X is oxo or thioxo; or a therapeutically acceptable salt, with an organic or inorganic base, of the compound of formula I having one or more carboxyls.

3. The compound of formula I, as claimed in claim 1, in which $R^1$ and $R^2$ each is hydrogen, $R^3$ is carboxy, acetyl or cyano, $R^4$ is hydrogen or 6-chloro and X is oxo or thioxo; or a therapeutically acceptable salt thereof with an organic or inorganic base.

4. 3-Carboxy-1,2-dihydro-2-oxocyclohepta[b]pyrrole-1-acetic acid, or its corresponding diethyl ester, as claimed in claim 1.

5. 1,2-Dihydro-2-oxocyclohepta[b]pyrrole-1-acetic acid, as claimed in claim 1.

6. 3-(Ethoxycarbonyl)-1,2-dihydro-2-oxocyclohepta[b]pyrrole-1-acetic acid, as claimed in claim 1.

7. 3-Carboxy-1,2-dihydro-2-thioxocyclohepta[b]pyrrole-1-acetic acid, or its corresponding diethyl ester, as claimed in claim 1.

8. 1,2-Dihydro-3-[(2,2-dimethyl-1-oxopropoxy)methoxycarbonyl]-2-oxocyclohepta[b]pyrrole-1-acetic acid (2,2-dimethyl-1-oxopropoxy)methyl ester, as claimed in claim 1.

9. 3-Acetyl-1,2-dihydro-2-oxocyclohepta[b]pyrrole-1-acetic acid, or its corresponding ethyl ester, as claimed in claim 1.

10. 3-Ethyl-1,2-dihydro-2-oxocyclohepta[b]pyrrole-1-acetic acid, or its corresponding ethyl ester, as claimed in claim 1.

11. 3-Carboxy-6-chloro-1,2-dihydro-2-oxocyclohepta[b]pyrrole-1-acetic acid, or its corresponding diethyl ester, as claimed in claim 1.

12. 6-Chloro-3-(ethoxycarbonyl)-1,2-dihydro-2-oxocyclohepta[b]-pyrrole-1-acetic acid, as claimed in claim 1.

13. 3-Acetyl-6-chloro-1,2-dihydro-2-oxocyclohepta[b]pyrrole-1-acetic acid, or its corresponding ethyl ester, as claimed in claim 1.

14. 3-Cyano-1,2-dihydro-2-oxocyclohepta[b]pyrrole-1-acetic acid, or its corresponding ethyl ester, as claimed in claim 1.

15. (3-Aminocarbonyl)-1,2-dihydro-2-oxocyclohepta[b]pyrrole-1-acetic acid, or its corresponding ethyl ester, as claimed in claim 1.

16. 2-(3-Ethoxycarbonyl-1,2-dihydro-2-2-oxocyclohepta[b]pyrrol-1-yl)butanedioic acid dimethyl ester, as claimed in claim 1.

17. 2-(3-Carboxy-1,2-dihydro-2-oxocyclohepta[b]pyrrol-1-yl)butanedioic acid, as claimed in claim 1.

18. 6-Chloro-3-{[(N-ethoxycarbonylmethyl-N-methyl)amino]-carbonyl}-1,2-dihydro-2-oxocyclohepta[b]pyrrole-1-acetic acid ethyl ester, as claimed in claim 1.

19. 6-Chloro-3-{[(N-carboxymethyl-N-methyl)amino]carbonyl}-1,2-dihydro-2-oxocyclohepta[b]pyrrole-1-acetic acid disodium salt, as claimed in claim 1.

20. A pharmaceutical composition for preventing or relieving diabetic complications in a diabetic mammal, which comprises a compound of claim 1, or a therapeutically acceptable salt thereof with an organic or inorganic base, and a pharmaceutically acceptable carrier.

21. A method of preventing or relieving a diabetic complication in a diabetic mammal, which comprises administering to said mammal an alleviating or prophylactic amount of a compound of claim 1, or a therapeutically acceptable salt thereof with an organic or inorganic base.

22. The method of claim 20 wherein the diabetic complication is selected from neuropathy, nephropathy, retinopathy and cataracts.

* * * * *